US012717166B2

(12) United States Patent
Haitani

(10) Patent No.: US 12,717,166 B2
(45) Date of Patent: Aug. 25, 2026

(54) METHOD FOR DETERMINING LENS FOR SPECTACLES OR LENS FOR CONTACT LENSES, AND SPECTACLE OR CONTACT LENS

(71) Applicant: Innochi inc., Oita (JP)

(72) Inventor: Takashi Haitani, Awaji (JP)

(73) Assignee: INNOCHI INC., Bungoono (JP)

( * ) Notice: Subject to any disclaimer, the term of this patent is extended or adjusted under 35 U.S.C. 154(b) by 327 days.

(21) Appl. No.: 18/561,638

(22) PCT Filed: Dec. 13, 2022

(86) PCT No.: PCT/JP2022/045781
§ 371 (c)(1),
(2) Date: Nov. 16, 2023

(87) PCT Pub. No.: WO2023/136021
PCT Pub. Date: Jul. 20, 2023

(65) Prior Publication Data

US 2025/0028188 A1 Jan. 23, 2025

(30) Foreign Application Priority Data

Jan. 12, 2022 (JP) ................................ 2022-002857

(51) Int. Cl.
*G02C 7/02* (2006.01)
*A61B 3/02* (2006.01)
*G02C 7/04* (2006.01)

(52) U.S. Cl.
CPC ................ *G02C 7/027* (2013.01); *A61B 3/02* (2013.01); *G02C 7/04* (2013.01); *G02C 2202/02* (2013.01)

(58) Field of Classification Search
CPC . G02C 7/027; G02C 7/04; G02C 7/14; G02C 2202/02; G02C 13/003; A61B 3/02; A61B 3/028
USPC .................................................... 351/159.01
See application file for complete search history.

(56) References Cited

U.S. PATENT DOCUMENTS

| | | | | |
|---|---|---|---|---|
| 4,850,690 | A * | 7/1989 | Parker | A61B 3/04 351/227 |
| 5,151,723 | A * | 9/1992 | Tajiri | G02C 7/043 351/159.41 |
| 2003/0107707 | A1 * | 6/2003 | Fisher | G02C 7/028 351/159.74 |
| 2014/0247424 | A1 | 9/2014 | Drobe | |
| 2018/0321517 | A1 * | 11/2018 | El-Hajal | A61B 3/111 |
| 2020/0393697 | A1 * | 12/2020 | Binder | G02C 7/086 |
| 2022/0304572 | A1 * | 9/2022 | Coveney | A61B 3/1015 |
| 2022/0308362 | A1 * | 9/2022 | Aikawa | G02C 7/027 |
| 2022/0354436 | A1 * | 11/2022 | Zakharov | G16H 50/30 |
| 2024/0339219 | A1 * | 10/2024 | Haitani | G02C 13/003 |

FOREIGN PATENT DOCUMENTS

| | | |
|---|---|---|
| JP | H7-100107 | 4/1995 |
| JP | 2002-202482 | 7/2002 |
| JP | 2003-075785 | 3/2003 |
| JP | 2008-212718 | 9/2008 |
| JP | 2014-059533 | 4/2014 |
| JP | 3209988 | 4/2017 |
| JP | 2020-536282 | 12/2020 |
| JP | 3232059 | 5/2021 |
| WO | WO 2020/225622 | 11/2020 |

* cited by examiner

*Primary Examiner* — William R Alexander
(74) *Attorney, Agent, or Firm* — COZEN O'CONNOR

(57) ABSTRACT

To provide a method for determining a lens for spectacles or a lens for contact that achieves a trunk balance.
There are included step S6 of measuring a load balance or a posture of a subject to be measured, and steps S7 to S10 of determining a lens for spectacles or a lens for contact lenses on the basis of a result of the measurement of the load balance or the posture.

12 Claims, 6 Drawing Sheets

METHOD FOR DETERMINING LENS FOR SPECTACLES OR LENS FOR CONTACT LENSES, AND SPECTACLE OR CONTACT LENS

PRIORITY CLAIM

This is a U.S. national stage of application No. PCT/JP2022/045781, filed on Dec. 13, 2022. Priority is claimed on Japanese Application No. JP 2022-002857, filed Jan. 12, 2022, the content of which is incorporated herein by reference.

TECHNICAL FIELD

The present invention relates to a method for determining a lens for spectacles or a lens for contact lenses appropriate for a subject to be measured, and a spectacle or a contact lens.

BACKGROUND ART

When a pair of spectacles is made or contact lenses are purchased, a visual function is measured from various viewpoints and appropriate lenses are determined.

CITATION LIST

Patent Literature

Patent Literature 1: JP H7-100107 A
Patent Literature 2: JP 2014-059533 A

SUMMARY OF INVENTION

Technical Problem

No matter how accurately the visual function is measured and the power of the lenses or the like is determined according to a result of the measurement, an uncomfortable feeling generated in the eyes and the body may not be solved.

An object of the present invention is to provide a method for determining a lens for spectacles or a lens for contact lenses capable of appropriately maintaining not only correction of visual acuity but also a trunk balance, and spectacles or contact lenses.

Solution to Problem

A method for determining a lens for spectacles according to a first invention includes the steps of: measuring a load balance of a subject to be measured; and determining a lens for spectacles or a lens for contact lenses on the basis of a result of the measurement of the load balance.

In a second invention, the step of measuring a load balance includes a step of measuring a left and right balance of loads, and the step of determining a lens includes a step of determining the power of a spherical lens for spectacles or a spherical lens for contact lenses on the basis of a result of the measurement of the left and right balance.

In a third aspect of the present invention, the step of measuring a load balance includes a step of measuring a twist of a body, and the step of determining a lens for spectacles or a lens for contact lenses includes a step of determining the power and axial degree of a cylindrical lens for spectacles or a cylindrical lens for contact lenses on the basis of a result of the measurement of the twist of the body.

In a fourth invention, the step of measuring a load balance includes a step of measuring a front and back balance of loads, and the step of determining a lens for spectacles or a lens for contact lenses includes a step of determining the power and direction of a prism lens for spectacles or a lens for contact lenses on the basis of a result of the measurement of the front and back balance of loads.

A fifth invention further includes a step of measuring a visual function of the subject to be measured, and the step of determining a lens for spectacles or a lens for contact lenses determines a lens for spectacles or a lens for contact lenses on the basis of a result of the measurement of the visual function and the result of the measurement of the load balance.

A method for determining a lens for spectacles or a lens for contact lenses according to a sixth invention includes the steps of: measuring a posture of a subject to be measured; and determining a lens for spectacles or a lens for contact lenses on the basis of a result of the measurement of the posture.

In a seventh invention, the step of measuring a posture includes a step of measuring a left and right inclination of the posture, and the step of determining a lens for spectacles or a lens for contact lenses includes a step of determining the power of the spherical lens for spectacles or a spherical lens for contact lenses on the basis of a result of the measurement of the left and right inclination of the posture.

In eighth invention, the step of measuring a posture includes a step of measuring a twist of a body, and the step of determining a lens for spectacles or a lens for contact lenses includes a step of determining the power and axial degree of a cylindrical lens for spectacles or a cylindrical lens for contact lenses on the basis of a result of the measurement of the twist of the body.

In a ninth invention, the step of measuring a posture includes a step of measuring a front and back inclination of the posture, and the step of determining a lens for spectacles or a lens for contact lenses includes a step of determining the power and direction of a prism lens for spectacles or a prism lens for contact lenses on the basis of a result of the measurement of the front and back inclination of the posture.

A tenth invention further includes a step of measuring a visual function of the subject to be measured, and the step of determining a lens for spectacles or a lens for contact lenses determines a lens for spectacles or a lens for contact lenses on the basis of a result of the measurement of the visual function and the result of the measurement of the posture.

A pair of spectacles according to an eleventh present invention include a lens for spectacles determined on the basis of a result of measurement of a load balance or a posture of a subject to be measured.

A contact lens according to a twelfth invention includes a lens for contact lenses determined on the basis of a result of measurement of a load balance or a posture of a subject to be measured.

Advantageous Effects of Invention

According to the first to ninth inventions, it is possible to determine a lens for spectacles or a lens for contact lenses capable of appropriately maintaining not only visual acuity but also a trunk balance.

According to the second and seventh present inventions, it is possible to determine a lens for spectacles or a lens for contact lenses capable of appropriately maintaining a left and right balance of loads of a subject to be measured.

According to the third and eighth inventions, it is possible to determine a lens for spectacles or a lens for contact lenses capable of eliminating a twist of a body of a subject to be measured.

According to the fourth and ninth inventions, it is possible to determine a lens for spectacles or a lens for contact lenses capable of appropriately maintaining a front and back balance of loads of a subject to be measured.

According to the fifth and tenth inventions, it is possible to determine a lens for spectacles or a lens for contact lenses capable of adjusting both a trunk balance and visual acuity.

According to the sixth and 11 inventions, it is possible to adjust a trunk balance of a person wearing a pair of spectacles or contact lenses and guides the person into a more comfortable state.

DESCRIPTION OF EMBODIMENTS

First Embodiment

Hereinafter, a first embodiment of the present invention will be described.

Figure 1:
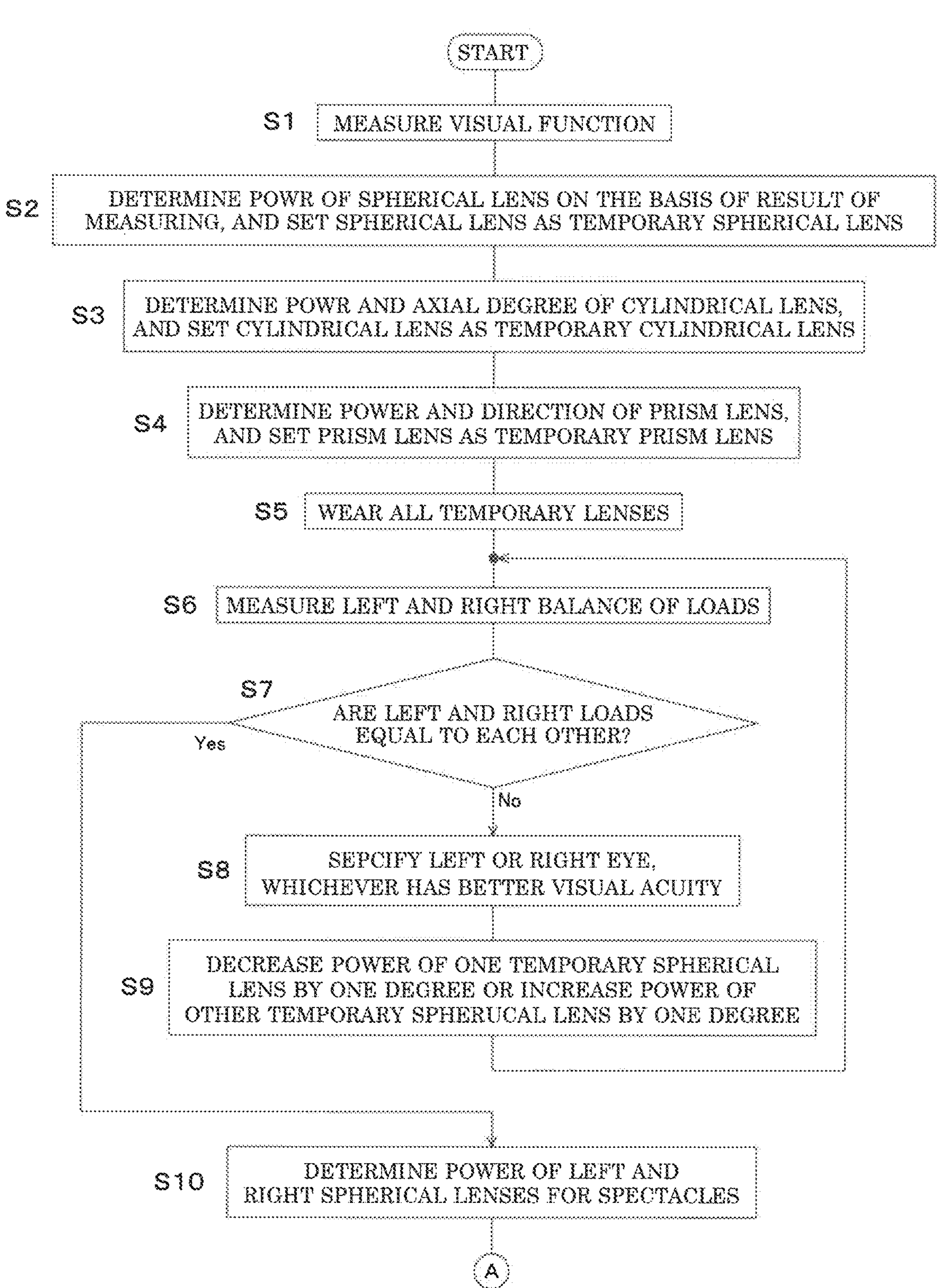
FIG. 1 is a flowchart illustrating a procedure until the power of a spherical lens for spectacles is determined in a first embodiment of the present invention.
Figure 2:
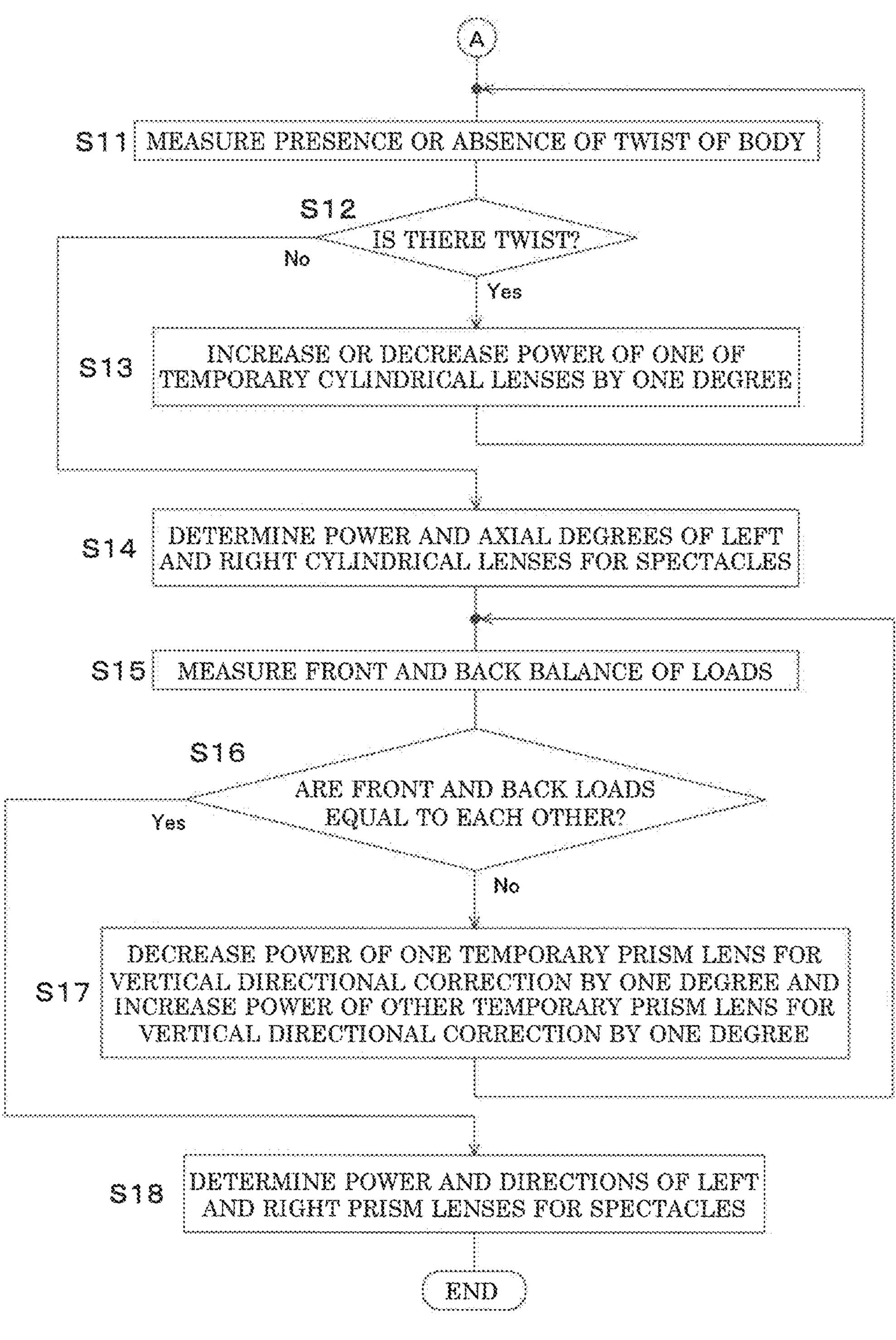
FIG. 2 is a flowchart illustrating a procedure for determining the power and axis of a cylindrical lens for spectacles and the power and direction of a prism lens in the first embodiment, following the flowchart of FIG. 1.
Figure 3:
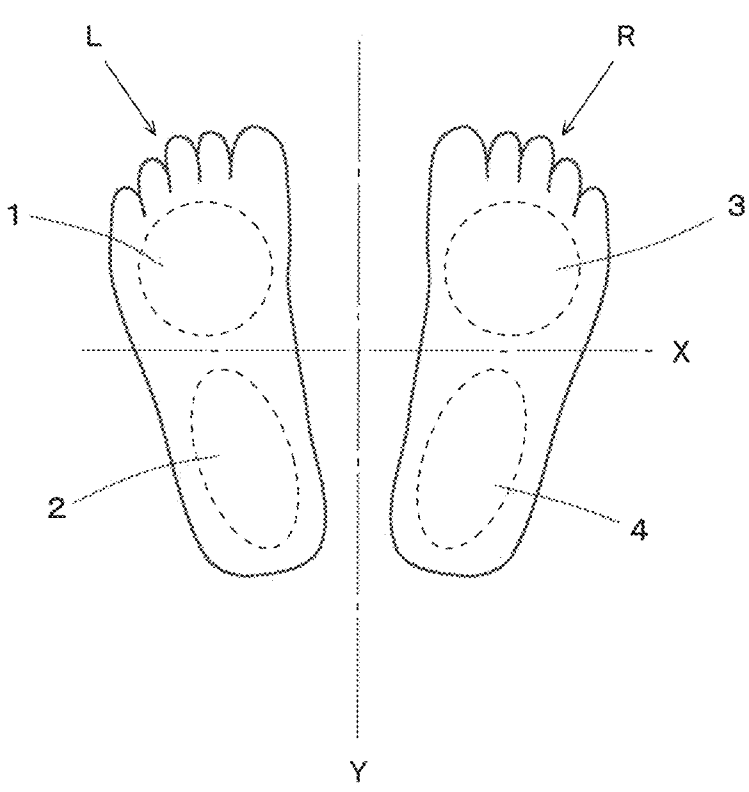
FIG. 3 is a diagram visualizing a load distribution of a subject to be measured.

Note that FIGS. 1 to 2 are a flowchart illustrating a procedure for determining a lens for spectacles in the first embodiment. FIG. 3 is a diagram visualizing a load balance of a subject to be measured.

In order to determine a lens for spectacles, as illustrated in FIG. 1, first, a visual function of the subject to be measured is measured (step S1). The measurement of the visual function is performed by a general ophthalmologist, a spectacles store, or the like, and is performed using, for example, a device as described in Patent Literature 1 or 2. Then, the degree of astigmatism or strabismus of the left and right eyes of the subject to be measured is measured in addition to the visual acuity thereof.

In step S2, the power of a spherical lens for spectacles is decided on the basis of a result of the measurement of the visual acuity obtained by the measurement, and the spherical lens is set as a temporary spherical lens. The spherical lens corrects a focal length of an eye of the subject to be measured, and when the power of the spherical lens is determined, it is possible to refer to not only a value measured by a measurement device but also a view and a feeling of the subject to be measured when a lens having different power is actually attached to and detached from a frame for testing.

After the temporary spherical lens is decided, in step S3, the power and axial degree of a cylindrical lens for spectacles for correcting astigmatism are decided, and the cylindrical lens for spectacles is set as temporary cylindrical lens.

When the power and axial degree of the temporary cylindrical lens are determined, the subject to be measured may be asked about his or her view and feeling in a state in which the temporary spherical lens and the temporary cylindrical lens are combined together and worn, and the power may be finely adjusted with reference to the view and feeling of the subject to be measured.

In step S4, the power and direction of a prism lens for spectacles for correcting astigmatism or strabismus by correcting the direction of the line of sight is decided, and the prism lens for spectacles is set as a temporary prism lens.

Note that in the first embodiment, as prism lenses, a prism lens for vertical directional correction, which corrects the vertical direction of the line of sight, and a prism lens for horizontal directional correction are individually worn to adjust the power. Here, the prism lens for vertical directional correction may be referred to as an up lens or a down lens, and the prism lens for horizontal directional correction may be referred to as an in lens or an out lens.

In step S5, all the left and right temporary lenses determined in the steps are worn. Then, if necessary, each temporary lens is finely adjusted according to the feeling and preference of the subject to be measured.

Steps S1 to S5 described above are performed by a general ophthalmologist or a spectacles store when a pair of spectacles is made.

In step S6, a left and right balance of loads of the subject to be measured is measured. The left and right balance of loads is a balance of loads acting on the left and right feet, and it is determined that the left and right balance is good when the magnitudes of both the loads are equal to each other. As a device for measuring such a load balance, a centroid oscillation meter, a foot pressure meter, a weight meter, or the like can be used. Here, a case where a foot pressure meter is used will be described.

For example, FIG. 3 is an image visualizing a load distribution of soles of the subject to be measured, the image being an image of output of the foot pressure meter in which the magnitudes of loads are displayed in colors in left and right foot molds L and R. The balance of loads can be determined from such an image. Specifically, it is determined whether the loads of the left and right feet are equal to each other between the left and right sides of a left and right center line Y passing through the center of both feet.

When the left and right loads are equal to each other in step S7, the process proceeds to step S10, and the power of a final spherical lens for spectacles is determined. The power of the spherical lens for spectacles determined here is the power of the temporary spherical lens worn by the subject to be measured at the time of step S10.

Meanwhile, when the left and right loads are not equal to each other, the process proceeds from step S7 to step S8, and the left or right eye, whichever has better visual acuity, is specified. The visual acuity is visual acuity in a state in which the temporary spherical lens determined in step S2 described above is worn.

In step S9, the power of one lens, that is, a temporary spherical lens having better visual acuity is decreased by one degree, or the power of the other lens, that is, a temporary spherical lens having worse visual acuity is increased by one degree. When the power of the temporary spherical lens is changed in this manner, the process returns to step S6 to measure the left and right balance of loads.

Then, the process proceeds to step S7, and repeats steps S6 to S9 until the left and right balance of loads is achieved. Then, when the left and right loads become equal to each other, the process proceeds to step S10, and the power of final left and right spherical lenses for spectacles is determined.

Note that in the first embodiment, in steps S8 and S9 described above, the power of the temporary spherical lens having better visual acuity is decreased or the power of the temporary spherical lens having worse visual acuity is increased. However, a procedure for adjusting the power of the temporary spherical lens is not limited to this. In steps S8 and S9, it is only necessary to adjust the power of any of the temporary spherical lenses so that the left and right loads become equal to each other. However, it has been experienced that in a case where there is a difference in visual acuity, the left and right balance of loads is often achieved by finely adjusting the power of the temporary spherical lens so that the difference is reduced as described above.

After the power of the spherical lens for spectacles is determined, the process proceeds to step S11 in FIG. 2.

In step S11, a twist of a body of the subject to be measured is measured with the foot pressure meter. The twist of the body can be determined from the load distribution of both feet. When the body is twisted, the magnitudes of front and back loads are opposite to each other on the left and right sides. For example, in a case where the body is twisted to the right side, a load in a left front area 1 in FIG. 3 is larger than a load in a left back area 2, and a load in a right front area 3 is smaller than a load in a right back area 4.

In a case where it is determined in step S12 that there is no twist, the process proceeds to step S14, and the power and axial degrees of the left and right temporary cylindrical lenses worn at that time are directly determined as the power and axial degrees of final cylindrical lenses for spectacles.

Meanwhile, if there is a twist, the process proceeds from step S12 to step S13.

In step S13, the power of one of the left and right temporary cylindrical lenses is increased by one degree or decreased by one degree, the process returns to step S11, and the twist of the body is measured again.

Then, in steps S11 to S13, the adjustment of the power of the temporary cylindrical lens is repeated until the twist is eliminated.

Note that in a case where the power of one of the temporary cylindrical lenses is increased in step S13, the power may be continuously increased until the twist is eliminated. In a case where the twist is not solved even when the power reaches a predetermined value, a step of decreasing the power of the temporary cylindrical lens determined in step S3 may be repeated. Alternatively, the power of the temporary cylindrical lens may be increased or decreased while a change in the magnitude of the twist is observed. In this process of adjusting the temporary cylindrical lens, a lens whose power is first adjusted may be either the right or left lens.

Furthermore, in the first embodiment, the axial degree of each temporary cylindrical lens is fixed, and only the power of the temporary cylindrical lens is adjusted. However, in a case where the twist of the body cannot be eliminated by adjusting the power, the axial degree can also be adjusted.

After the power and axial degrees of the final left and right cylindrical lens for spectacles are determined in step S14, the process proceeds to step S15, and a front and back balance of loads of the subject to be measured is measured. The front and back balance of loads is also measured by the foot pressure meter in a manner similar to that as described above. In FIG. 3, it is determined whether the loads in the left front area 1 and right front area 3 on a front side of a front and back center line X of the left and right foot molds L and R are equal to the loads in the left back area 2 and right back area 4 on a back side (step S16). If the front and back loads are equal to each other, the process proceeds to step S18, and the power and direction of the temporary prism lens worn at that time are directly determined as the power and direction of the prism lens for spectacles. Note that the power and direction of the left and right prism lens for spectacles determined in step S18 are coincided with a correction value of the temporary prism lens for horizontal directional correction that is not adjusted.

Meanwhile, in a case where it is determined in step S16 that the front and back loads are not equal to each other and the front and back balance is lost, the process proceeds to step S17. Then, while the direction of the temporary prism lens for vertical directional correction is fixed, the power of one temporary prism lens is decreased by one degree and the power of the other temporary prism lens is increased by one degree. Then, the process returns to step S15, and the front and back balance of loads is measured again.

Then, steps S15 to S17 are repeated until the front and back loads become equal to each other.

Following the above steps determines characteristic values such as the power, axial degree, direction, and the like of the lens for spectacles, at which the left and right balance of loads and the front and back balance of loads are achieved and the twist of the body is eliminated.

Then, the determined characteristic values of each lens are integrated to make left and right lenses for spectacles.

Therefore, if a pair of spectacles is made using the lenses for spectacles determined by a determination method of the first embodiment, a spectacle wearer can appropriately maintain a trunk balance while improving a visual function, and is guided to a more comfortable life.

Note that, in step S7 or step S16 described above, not only in a case where the left and right loads or the front and back loads are completely equal to each other but also in a case where the left and right loads or the front and back loads are substantially equal to each other, it may be determined that the loads are equal to each other, and in step S12, a slight twist is determined as no twist.

As described above, it is considered that a reason why the trunk balance is adjusted by appropriate lenses for spectacles is that the movement of muscles around eyeballs used to supplement the visual function has various effects on other parts of the body.

In the first embodiment, the power and the like of three types of lenses such as the spherical lens, the cylindrical lens, and the prism lens are determined as lenses for spectacles. However, it is not necessarily necessary to determine the power and the like of the three types of lenses. For example, only the spherical lens may be adjusted to particularly adjust the left and right balance, only the cylindrical lens may be adjusted to eliminate the twist of the body, or only the prism lens may be adjusted to adjust the front and back balance.

Second Embodiment

A second embodiment will be described with reference to FIG. 4.

Figure 4:
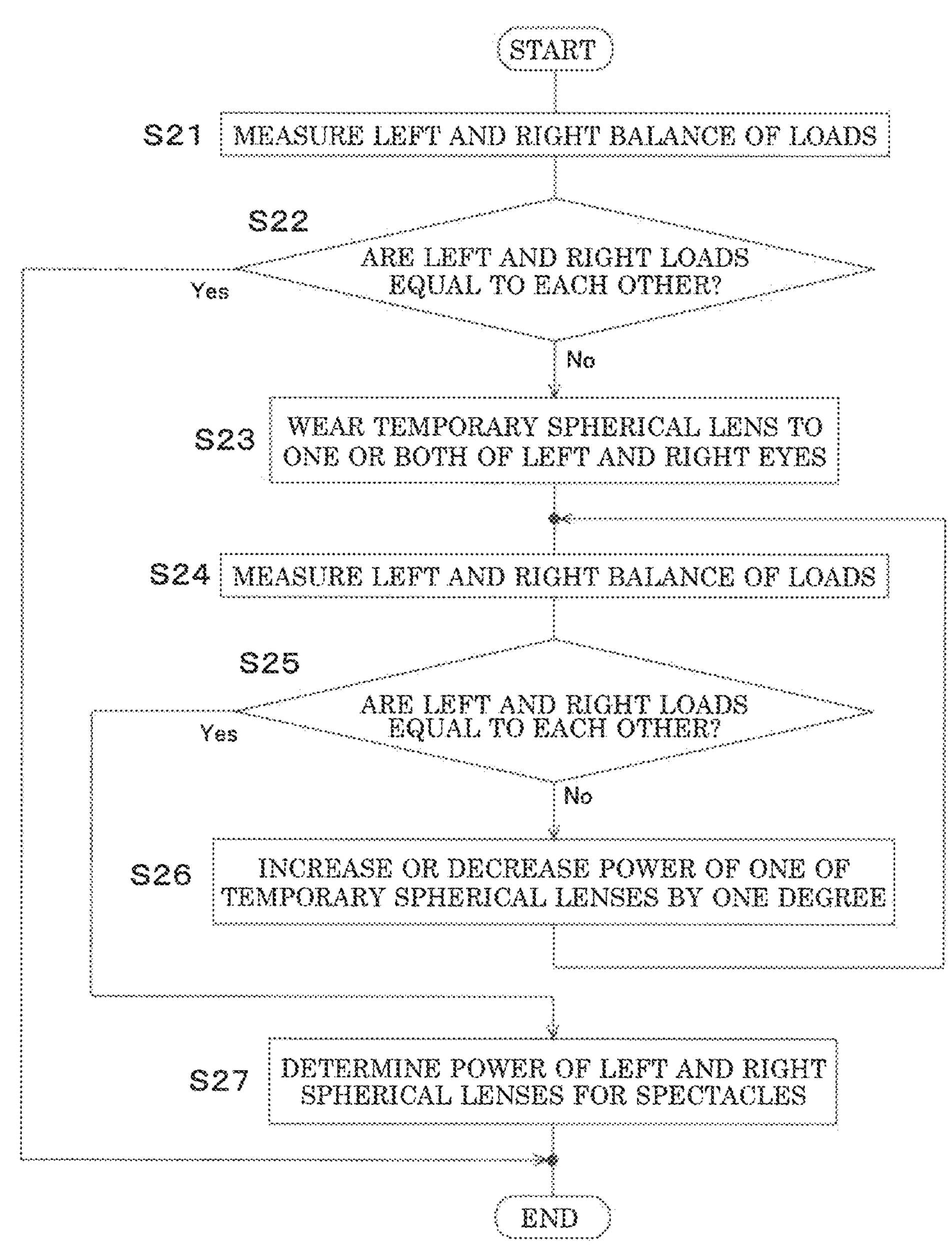
FIG. 4 is a flowchart of a second embodiment.

The second embodiment is a method for determining left and right spherical lenses for spectacles without measuring a visual function, and FIG. 4 is a flowchart of the second embodiment.

In the second embodiment, first, a left and right balance of loads of a subject to be measured is measured in step S21, and it is determined whether left and right loads are equal to each other (step S22). A foot pressure meter is used to measure a balance of loads as in the first embodiment.

When the left and right loads are equal to each other in step S22, work is finished. This means that the subject to be measured does not need a spherical lens for adjusting the left and right balance.

Meanwhile, when the left and right loads are not equal to each other, the process proceeds from step S22 to step S23, and a temporary spherical lens is worn to one or both of left and right eyes. The temporary spherical lens worn here has relatively low power.

When the subject to be measured wears the temporary spherical lens, the left and right balance of loads is measured again in step S24.

When the left and right loads are equal to each other, the process proceeds from step S25 to step S27, and the power of the spherical lens for spectacles is determined. The power of the spherical lens for spectacles determined here is the power of the temporary spherical lens worn by the subject to be measured at that time.

Meanwhile, in a case where the left and right loads are not equal to each other, the process proceeds to step S26, the power of one of the temporary spherical lenses is increased by one degree or decreased by one degree, and the process returns to step S24 to measure the left and right balance of loads.

Then, steps S24 to S26 are repeated until the left and right balance of loads is achieved. When the left and right loads become equal to each other, the process proceeds to step S27, and the power of the final left and right spherical lenses for spectacles is determined, and the spherical lenses are used as lenses for spectacles.

In the second embodiment, the lens for spectacles is determined on the basis only of a result of the measurement of the left and right balance of loads without measuring a visual function. When a pair of spectacles using such lenses for spectacles are worn, a left and right balance of a trunk can be adjusted.

Third Embodiment

Figure 5:
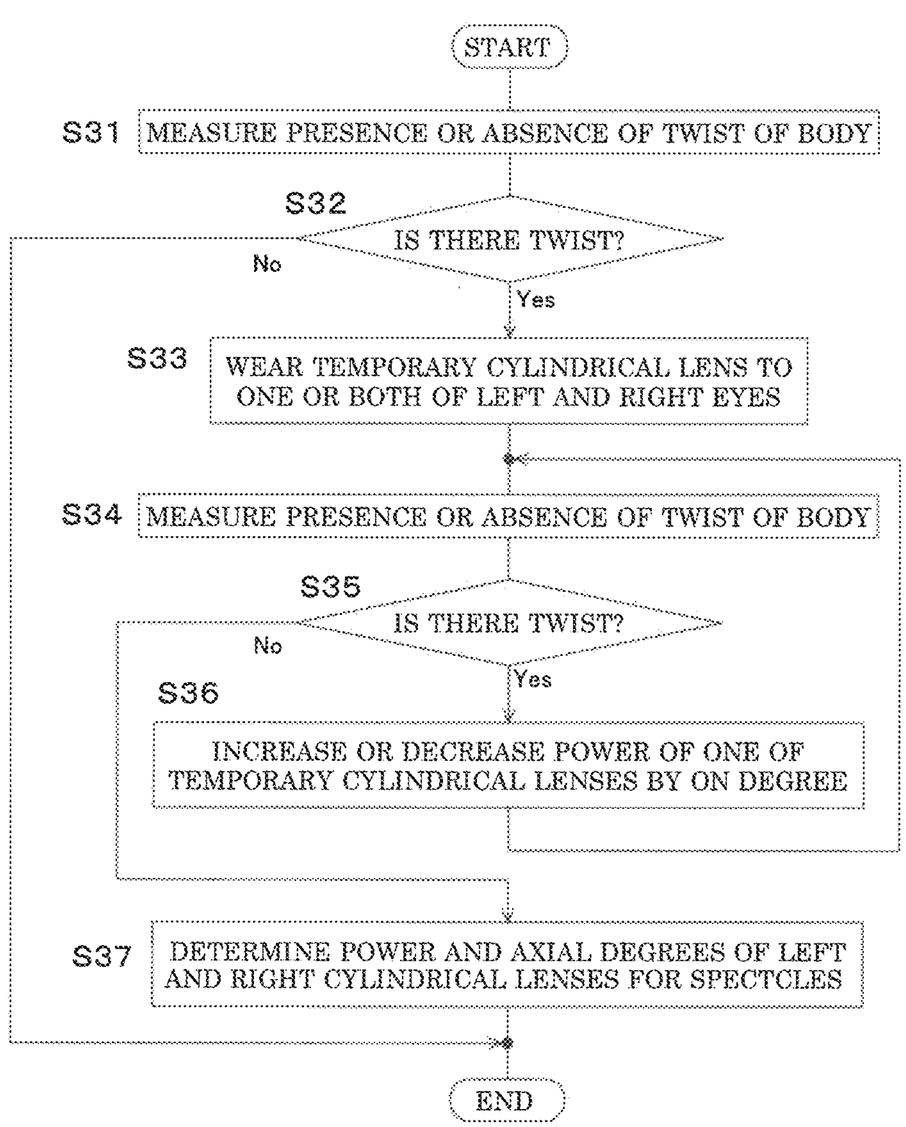
FIG. 5 is a flowchart of a third embodiment.

Next, there will be described a third embodiment in which a cylindrical lens for spectacles for improving a twist of a body of a subject to be measured is determined. FIG. 5 is a flowchart of the third embodiment.

In step S31 of FIG. 5, the twist of the body of the subject to be measured is measured in a manner similar to that in step S11 of the first embodiment.

In a case where it is determined in step S32 that there is no twist, the subject to be measured does not need the cylindrical lens for spectacles, and thus work is finished.

When there is a twist of the body of the subject to be measured, the process proceeds from step S32 to step S33, and a temporary cylindrical lens is worn to one or both of left and right eyes. This temporary cylindrical lens has low power. In addition, an axial degree is also temporarily determined.

When the subject to be measured wears the temporary spherical lens, the twist of the body of the subject to be measured is measured again in step S34.

In a case where there is no twist of the body, the process proceeds from step S35 to step S37, and the power and axial degrees of the left and right cylindrical lens for spectacles are determined. The power and axial degree of the cylindrical lens for spectacles determined here is the power and axial degree of the temporary cylindrical lens worn by the subject to be measured at that time.

Meanwhile, if there is a twist, the process proceeds from step S35 to step S36.

In step S36, the power of one of the left and right temporary cylindrical lenses is increased by one degree or decreased by one degree, the process returns to step S34, and the twist of the body is measured again.

Then, in steps S34 to S36, the adjustment of the power of the temporary cylindrical lens is repeated until the twist is eliminated.

Note that in a case where the power of one of the temporary cylindrical lenses is increased in step S36, the power may be continuously increased until the twist is eliminated. In a case where the twist is not solved even when the power reaches a predetermined value, a step of decreasing the power of the temporary cylindrical lens determined in step S33 may be repeated. Alternatively, the power of the temporary cylindrical lens may be increased or decreased while a change in the magnitude of the twist is observed. In this process of adjusting the temporary cylindrical lens, a lens whose power is first adjusted may be either the right or left lens.

Furthermore, also in the third embodiment, the axial degree of each temporary cylindrical lens is fixed, and only the power of the temporary cylindrical lens is adjusted. However, in a case where the twist of the body cannot be eliminated by adjusting the power, the axial degree can be adjusted.

Fourth Embodiment

There will be described a fourth embodiment for determining a prism lens for spectacles for adjusting a front and back balance of a subject to be measured.

Figure 6:
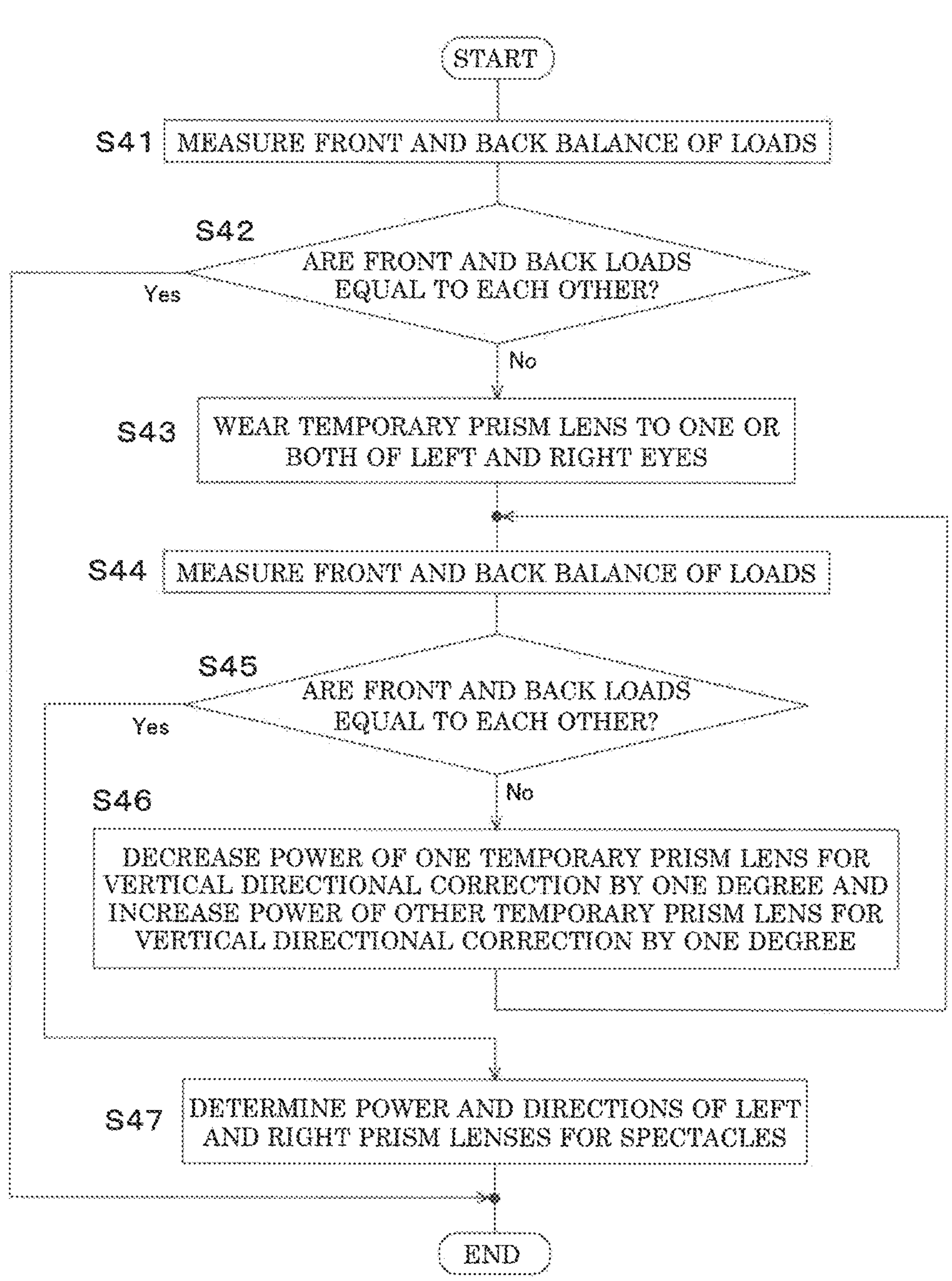
FIG. 6 is a flowchart of a fourth embodiment.

FIG. 6 is a flowchart of the fourth embodiment.

In step S41 of FIG. 6, a front and back balance of loads of the subject to be measured is measured in a manner similar to that in step S15 of the first embodiment. In step S42, it is determined whether front and back loads are equal to each other. If the front and back loads are equal to each other, the subject to be measured does not need the prism lens for spectacles, and thus work is finished.

Meanwhile, in a case where it is determined that the front and back loads are not equal to each other in step S42, the process proceeds to step S43, and a temporary prism lens is worn to one or both of left and right eyes. The temporary prism lens has low power, and a direction of the temporary prism lens is also temporarily decided. Here, a temporary prism lens for vertical directional correction is used.

When the subject to be measured wears the temporary prism lens in step S43, the front and back balance of loads is measured again in step S44.

If the front and back loads are equal to each other, the process proceeds from step S45 to step S47, and the power and directions of the left and right prism lenses for spectacles are finally determined. The power and directions of the prism lenses for spectacles determined here are the power and directions of the temporary prism lenses worn by the subject to be measured at that time.

Meanwhile, in a case where it is determined in step S45 that the front and back loads are not equal to each other, the power of one temporary prism lens for vertical directional correction is decreased by one degree, and the power of the other temporary prism lens is increased by one degree in step S46. Returning to step S44, steps S44 to S46 are repeated until the front and back loads become equal to each other, and when the front and back loads become equal to each other, the power and directions of the left and right prism lenses for spectacles are determined in step S47.

Following the above steps determines the left and right prism lenses for spectacles capable of adjusting the front and back balance of the subject to be measured. Note that although the above description describes an example of adjusting only the power of the prism lens for vertical directional correction, the direction may be adjusted as necessary while the front and back balance of loads of the subject to be measured is checked.

OTHER EMBODIMENTS

The second embodiment is a method for determining a lens for spectacles capable of improving a left and right balance of loads. The third embodiment is a method for determining a lens for spectacles capable of improving a twist of a body. The fourth embodiment is a method of determining a lens for spectacles capable for improving a front and back balance of loads. However, it is also possible to combine a plurality of these methods to integrate characteristic values of a lens determined in each flow to determine a lens for spectacles that further improves a trunk balance.

In addition, a step of measuring a visual function of a subject to be measured may be added, and a lens for spectacles may be finally determined by combining a result of the measurement of a balance of loads and a result of the measurement of the visual function. When the result of the measurement of the visual function is combined, improvement of the visual function can be expected together with improvement of the trunk balance.

Then, the step of measuring a visual function may be before or after a step of measuring a balance of loads. In a case where the measurement of the visual function is performed first, a temporary lens for spectacles is determined on the basis of a result of the measurement of the visual function, and a balance of loads is measured in a state in which the temporary lens for spectacles is worn, as in the first embodiment illustrated in FIG. 1.

In addition, in a case where the measurement of the visual function is performed after the flows of FIGS. 4 to 6, a lens for spectacles finally determined in each flow of FIGS. 4 to 6 is set as a temporary lens. After that, adjustment is performed on the basis of a result of the measurement of the visual function, and then a final lens for spectacles is determined.

In the first to fourth embodiments, when the power of the lens is adjusted, the power is increased or decreased by one degree, but the amount of an increase or decrease in the power is not limited to one degree.

In the embodiments, in the step of determining the power and axial degree of the cylindrical lens, at least one of the power and the axial degree may be determined. Also, as for the prism lens, it is only necessary to determine at least one of the power and the direction.

Then, a means for measuring a load balance is not limited to the foot pressure meter capable of measuring a load distribution as described above. For example, it is possible to use a weight meter, a centroid oscillation meter, or the like disposed separately in the front, back, left, and right, and it is also possible to determine a balance of loads and a twist of a body in a state in which a subject to be measured is on a balance board.

When a centroid position is specified by a centroid oscillation meter or the like, the balance of loads can be determined by the centroid position. For example, when a centroid is located on the left and right center line Y (see FIG. 3), it can be determined that left and right loads are equal to each other and a left and right balance is good. When a centroid is located on the front and back center line X, it can be determined that front and back loads are equal to each other and a front and back balance is good. Furthermore, it is also possible to determine a twist, inclination, and the like of the body from the standing appearance of the subject to be measured.

In the embodiments, the measurement is performed with the subject to be measured in a standing position. However, a balance in a sitting position may be measured, and a lens for spectacles may be determined on the basis of a result of the measurement. A balance of loads in the sitting position is measured in a manner similar to that in the case of the standing position. For example, a weight meter may be placed under a chair on which the subject to be measured is seated, or a centroid oscillation meter may be placed on a seat surface. In the case of the sitting position, a left and right balance can be measured on the basis of magnitudes of loads acting on left and right ischial bones.

In addition, instead of measuring the balance of loads, a posture of the subject to be measured may be analyzed, and a lens for spectacles may be determined on the basis of a result of the analysis.

The posture of the subject to be measured is analyzed by a posture analysis device equipped with posture analysis software, and a lens for spectacles is determined so as to approach a preset target posture.

Specifically, among the steps described above, the step of measuring a balance of loads is replaced with a step of measuring a posture. Then, in a case where the posture is inclined to the left and right, a spherical lens is adjusted, and in a case where the body is twisted, a cylindrical lens is adjusted, and in a case where the front and back balance is poor, a prism lens is adjusted to finally determine a lens for spectacles, whereby the posture is approached to the target posture.

The target posture may be not only a well-balanced posture but also a posture advantageous for the living environment of the subject to be measured or the like. In the case of an athlete, a posture suitable for a specific sport can be set as a target posture.

According to the embodiments described above, it is possible to determine a lens for spectacles capable of appropriately maintaining the trunk balance of the subject to be measured.

In addition, it is also possible to determine a lens for contact lenses instead of a lens for spectacles by the same procedures as those in the first to fourth embodiments. That is, a lens having the same characteristics as those of a lens for spectacles determined as described above is used as a contact lens, it is possible to adjust balance of a wearer and guide the wearer into a comfortable state.

INDUSTRIAL APPLICABILITY

A healthier life can be achieved with a pair of spectacles.

REFERENCE SIGNS LIST

L Left foot mold
R Right foot mold
1 Left front area
2 Left back area
3 Right front area
4 Right back area Y Left and right center line X Front and back center line

The invention claimed is:

1. A method for determining a lens for spectacles or a lens for contact lenses, the method comprising the steps of:

measuring a load balance of a subject to be measured; and determining the lens for the spectacles or the lens for the contact lenses on the basis of a result of the measurement of the load balance;

wherein the step of measuring includes a step of measuring a left and right balance of loads, and the step of determining includes a step of determining power of a spherical lens for the spectacles or a spherical lens for the contact lenses on the basis of a result of the measurement of the left and right balance.

2. The method for determining a lens for spectacles or a lens for contact lenses according to claim 1, further comprising:

measuring a visual function of the subject to be measured, wherein the step of determining comprises determining the lens for the spectacles or the lens for the contact lenses on the basis of a result of the measurement of the visual function and the result of the measurement of the load balance.

3. A method for determining a lens for spectacles or a lens for contact lenses, the method comprising the steps of:

measuring a load balance of a subject to be measured; and determining the lens for the spectacles or the lens for the contact lenses on the basis of a result of the measurement of the load balance, wherein the step of measuring the load balance includes a step of measuring a twist of a body, and the step of determining the lens for spectacles or the lens for contact lenses includes a step of determining power and an axial degree of a cylindrical lens for the spectacles or a cylindrical lens for the contact lenses on the basis of a result of the measurement of the twist of the body.

4. The method for determining a lens for spectacles or a lens for contact lenses according to claim 3, further comprising the steps of:

measuring a visual function of the subject to be measured, wherein the step of determining comprises determining the lens for the spectacles or the lens for the contact lenses on the basis of a result of the measurement of the visual function and the result of the measurement of the load balance.

5. A method for determining a lens for spectacles, the method comprising the steps of:

measuring a load balance of a subject to be measured; and determining the lens for the spectacles on the basis of a result of the measurement of the load balance, wherein the step of measuring the load balance includes a step of measuring a front and back balance of loads, and the step of determining the lens for the spectacles includes a step of determining power and a direction of a prism lens for spectacles on the basis of a result of the measurement of the front and back balance.

6. The method for determining a lens for spectacles according to claim 5, further comprising the step of:

measuring a visual function of the subject to be measured, wherein the step of determining comprises determining the lens for the spectacles on the basis of a result of the measurement of the visual function and the result of the measurement of the load balance.

7. A method for determining a lens for spectacles or a lens for contact lenses, the method comprising the steps of:

measuring a posture of a subject to be measured; and determining a lens for spectacles or a lens for contact lenses on the basis of a result of the measurement of the posture, wherein the step of measuring a posture includes a step of measuring a left and right inclination of the posture, and the step of determining a lens for spectacles or a lens for contact lenses includes a step of determining power of a spherical lens for spectacles or a spherical lens for contact lenses on the basis of a result of the measurement of the left and right inclination of the posture.

8. The method for determining a lens for spectacles or a lens for contact lenses according to claim 7 wherein, the method further comprising the step of:

measuring a visual function of the subject to be measured, wherein the step of determining comprises determining a lens for spectacles or a lens for contact lenses on the basis of a result of the measurement of the visual function and the result of the measurement of the posture.

9. A method for determining a lens for spectacles or a lens for contact lenses, the method comprising the steps of measuring a posture of a subject to be measured; and determining a lens for spectacles or a lens for contact lenses on the basis of a result of the measurement of the posture, wherein the step of measuring a posture includes a step of measuring a twist of a body, and the step of determining a lens for spectacles or a lens for contact lenses includes a step of determining power and an axial degree of a cylindrical lens for spectacles or a cylindrical lens for contact lenses on the basis of a result of the measurement of the twist of the body.

10. The method for determining a lens for spectacles or a lens for contact lenses according to claim 9 wherein, the method further comprising the step of:

measuring a visual function of the subject to be measured, wherein the step of determining is performed on the basis of a result of the measurement of the visual function and the result of the measurement of the posture.

11. The method for determining a lens for spectacles, the method comprising the steps of:

measuring a posture of a subject to be measured; and determining a lens for spectacles or a lens for contact lenses on the basis of a result of the measurement of the posture, wherein the step of determining a lens for spectacles includes a step of determining power and a direction of a prism lens for spectacles on the basis of a result of the measurement of the front and back inclination of the posture.

12. The method according to claim 11, further comprising measuring a visual function of the subject to be measured, wherein the step of determining is performed on the basis of a result of the measurement of the visual function and the result of the measurement of the posture.

* * * * *